United States Patent [19]

Hauck et al.

[11] 4,029,676
[45] June 14, 1977

[54] ESTERS OF TETRAHYDRONAPHTHYLOXY-AMINO-PROPANOLS

[75] Inventors: Frederic P. Hauck, Somerville; Christopher M. Cimarusti, Hamilton; Venkatachala L. Narayanan, Hightstown, all of N.J.

[73] Assignee: E. R. Squibb & Sons, Inc., Princeton, N.J.

[22] Filed: Nov. 6, 1975

[21] Appl. No.: 629,734

Related U.S. Application Data

[63] Continuation-in-part of Ser. No. 203,865, Dec. 1, 1971, Pat. No. 3,935,267, which is a continuation-in-part of Ser. No. 48,458, June 22, 1970, abandoned.

[52] U.S. Cl. .................. 260/343.7; 260/348 C; 260/348 R; 260/404; 260/404.5; 260/472; 260/473 R; 260/477; 260/490; 260/570.7; 424/280; 424/308; 424/309; 424/311; 424/312
[51] Int. Cl.² .............. C07C 93/00; C07D 307/62
[58] Field of Search ....... 260/490, 477, 404, 404.5, 260/472, 343.7, 570.7, 473 R

[56] References Cited

FOREIGN PATENTS OR APPLICATIONS 2,130,393  12/1971  Germany .................. 260/490
2,258,995  12/1972  Germany .................. 260/490

*Primary Examiner*—Vivian Garner
*Attorney, Agent, or Firm*—Lawrence S. Levinson; Merle J. Smith; Donald J. Barrack

[57] ABSTRACT

Compounds having the formula

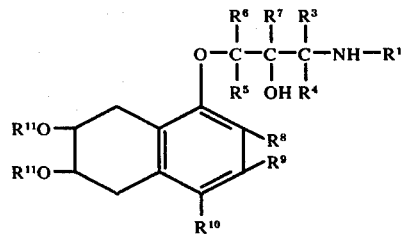

wherein $R^1$ is lower alkyl; $R^3$, $R^4$, $R^5$, $R^6$, and $R^7$ are the same or different and are hydrogen or lower alkyl; $R^8$, $R^9$, and $R^{10}$ are the same or different and are hydrogen, lower alkyl, lower alkoxy or cycloalkyl; and $R^{11}$ is acyl; are useful in the treatment of coronary diseases.

6 Claims, No Drawings

ESTERS OF TETRAHYDRONAPHTHYLOXY-AMINO-PROPANOLS

This application is a continuation-in-part of United States patent application Ser. No. 203,865, filed Dec. 1, 1971, issued as U.S. Pat. No. 3,935,267 on Jan. 27, 1976, which is a continuation-in-part of U.S. Patent application Ser. No. 48,458, filed June 22, 1970, and now abandoned.

SUMMARY OF THE INVENTION

This invention relates to new chemical compounds of the formula

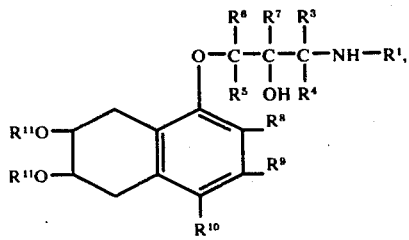

and salts of such compounds. In formula I, and throughout the specification, the symbols are as defined below.

$R^1$ can be lower alkyl;

$R^3, R^4, R^5, R^6$, and $R^7$ can be the same or different and can be hydrogen or lower alkyl;

$R^8$, $R^9$, and $R^{10}$ can be the same or different and can be hydrogen, lower alkyl, monocyclic aryl-lower alkyl, lower alkoxy, carboxy or monocyclic cycloalkyl; and $R^{11}$ can be acyl.

The term "lower alkyl" as used throughout the specification, includes both straight and branched chain radicals of up to and including eight carbon atoms, e.g., methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like.

The term "lower alkoxy" as used throughout the specification, includes straight and branched chain radicals of the structure RO— wherein R includes any of the above lower alkyl groups.

The term "monocyclic aryl", as used throughout the specification, includes phenyl and phenyl substituted with lower alkyl, lower alkoxy, halogen or nitro groups. Exemplary substituted phenyl groups are lower alkyl phenyl (e.g., o-, m-, or p-tolyl, ethylphenyl, butylphenyl and the like); di(lower alkyl)phenyl (e.g., 2,4-dimethylphenyl, 3,5-diethylphenyl, and the like); halophenyl (e.g., chlorophenyl, bromophenyl, iodophenyl, or fluorophenyl); o-, m- or p-nitrophenyl; dinitrophenyl (e.g., 3,5-dinitrophenyl, 2,6-dinitrophenyl, and the like); and trinitrophenyl (e.g., picryl).

The term "monocyclic aryl-lower alkyl", as used throughout the specification, refers to lower alkyl groups (as defined above) substituted with a monocyclic aryl group (as defined above). Included within the term are benzyl and phenethyl.

The term "acyl", as used throughout the specification, refers to fatty acid radicals having the formula

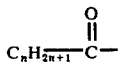

wherein $n$ is an integer of from 1 to 11 (e.g., acetyl, propionyl, butyryl, isobutyryl, hexanoyl, heptanoyl, decanoyl, dodecanoyl, and the like); acyl groups derived from monocyclic aryl carboxylic acids, i.e., groups having the formula

wherein X is monocyclic aryl as defined above (e.g., phenyl, o-tolyl, p-nitrophenyl, and the like); and acyl groups derived from aralkanoic acids, i.e., groups having the formula

wherein Z is monocyclic aryl-lower alkyl as defined above (e.g., benzyl, 3-phenylpropyl, 3-(p-chlorophenyl)butyl, and the like).

The term "monocyclic cycloalkyl", as used throughout the specification, refers to cycloalkyl groups having 3 to 6 ring members (e.g., cyclopropyl, cyclobutyl, cyclopentyl, and cyclohexyl).

The compounds of formula I form acid addition salts with inorganic and organic acids. These acid addition salts frequently provide useful means for isolating the products from reaction mixtures by forming the salt in a medium in which it is insoluble, and then neutralizing the salt with a base such as sodium hydroxide to obtain the free base. Any other salt may then be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicyclate, methanesulfonate, benzenesulfonate, toluenesulfonate, and the like. Quaternary ammonium salts are also formed, e.g., by reacting the free base with an alkylating agent such as a lower alkyl halide (e.g., methyl chloride, ethyl bromide, or the like), a lower alkyl sulfate (e.g., methyl sulfate), a monocyclic aryllower alkyl halide (e.g., benzyl chloride) or a monocyclic aryllower alkyl sulfate (e.g., benzyl sulfate), or the like.

Those compounds wherein $R^3, R^4, R^5, R^6, R^7, R^8, R^9$, and $R^{10}$ are all hydrogen are preferred.

The compounds of this invention are useful as antifibrillatory agents, for example, in arresting cardiac arrhythmia in mammals, e.g., by inhibition of beta adrenergic receptors in the myocardium. For this purpose a compound of formula 1 or a physiologically acceptable acid addition salt may be incorporated in a conventional dosage form such as a tablet capsule, elixir, injectable or the like along with the necessary carrier material, excipient, lubricant, buffer, or the like. Single or divided doses of about 5 to 25 mg/kg, preferably about 4 to 10 mg/kg, two to four times daily may be administered in dosage forms as described above.

Examples of compounds falling within the present invention include, but are not limited to, the following:

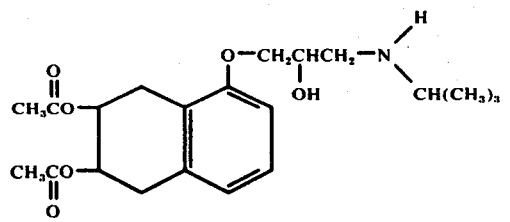

1.

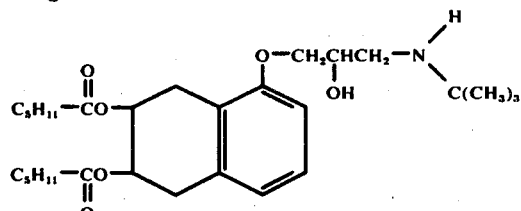

2.

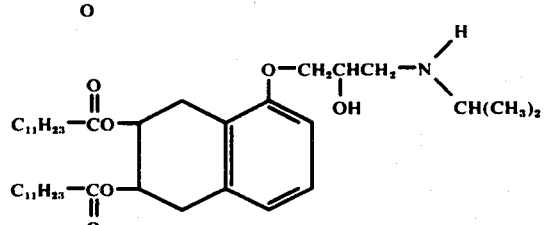

3.

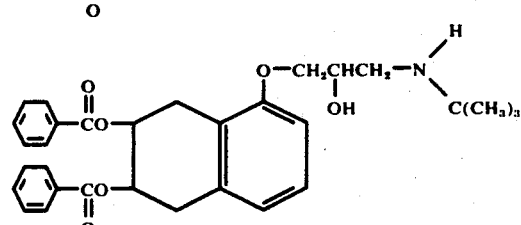

4.

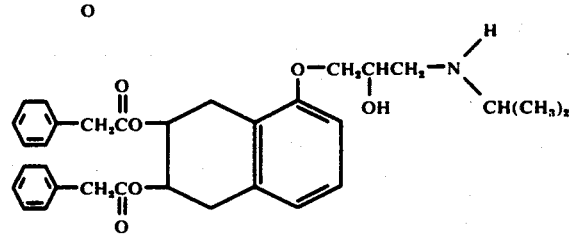

5.

The compounds of formula I are prepared from the corresponding 1,2,3,4-tetrahydro-2,3-naphthalenediol having the formula

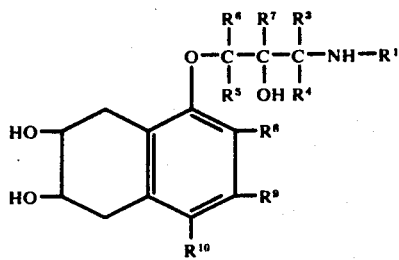

II

The procedure comprises first protecting the hydroxy group in the aminopropoxy side chain of a compound of formula II, acylating the remaining two hydroxy groups, and finally, removing the protecting group.

Various means for protecting the hydroxy group in the aminopropoxy side chain of a compound of formula II will be apparent to the practitioner of this invention. An exemplary method comprises reacting a compound of formula II with an aldehyde having the formula $$R^{12}CHO \qquad (III)$$

wherein $R^{12}$ is lower alkyl or monocyclic aryl to yield an oxazolidine derivative having the formula

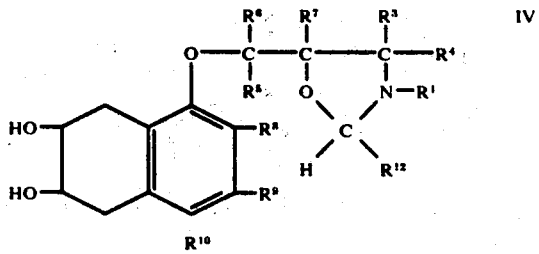

IV

The reaction can be run in an organic solvent, preferably at the reflux temperature of the solvent.

An oxazolidine derivative of formula IV can be acylated with an acid anhydride having the formula $$(R^{11})_2O \qquad (V)$$

or an acid chloride having the formula $$R^{11}\text{-Cl} \qquad (VI)$$

using procedures well known in the art to yield a compound having the formula

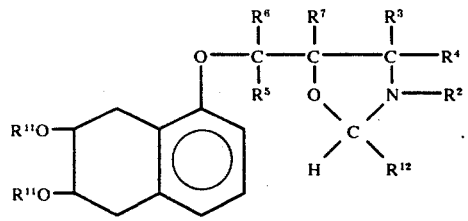

Catalytic reduction of a compound of formula VII using gaseous hydrogen and a catalyst such as platinum oxide or palladium yields the corresponding compound of formula I.

The compounds of formula I include those wherein the two acyloxy groups ($R^{11}O-$) are in the cis and in the trans configuration. Depending on which configuration it is desired to prepare, the corresponding 2,3-trans (or cis)-1,2,3,4-tetrahydro-5-[2-hydroxy-3-(alkylamino)propoxy]-2,3-naphthalenediol of formula II is used as the precursor.

A 2,3-trans (or cis)-1,2,3,4-tetrahydro-5-[2-hydroxy-3-(alkylamino)propoxy]-2,3-naphthalenediol of formula II can be prepared by first reducing a naphthol having the formula

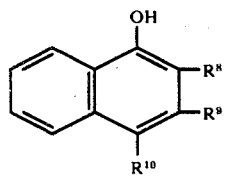

with a metal such as sodium or lithium in liquid ammonia containing an alkanol such as ethanol, isopropanol, t-butanol or the like [e.g., by the procedure described in Organic Synthesis Coll. Vol. 4, page 887 (1963)] to obtain a 5,8-dihydronaphthol of the formula

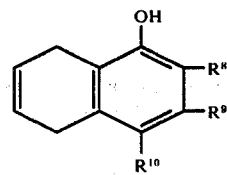

A 5,8-dihydronaphthol of formula IX can be converted to the corresponding acetate having the formula

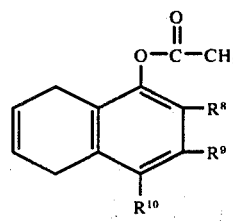

by dissolving it in acetic anhydride and an organic base such as pyridine.

A trans-5,6,7,8-tetrahydro-1,6,7-naphthalenetriol can be prepared from an acetate of formula X by dissolving the acetate in acetic acid, and then treating the solution with from about 2 to about 4 equivalents of silver acetate and from about 1 to about 2 equivalents of iodine. The mixture is then heated at a temperature of from about 80 to about 120° C for a period of from about 1 to about 24 hours under nitrogen, to yield a trans-5,6,7,8-tetrahydro-1,6,7-naphthalenetriol having the formula

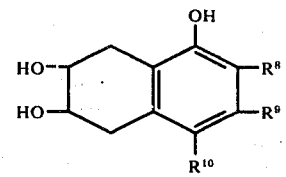

after basic hydrolysis.

A compound of formula XI can be converted to a 2,3-trans-1,2,3,4-tetrahydro-5-[2,3-(epoxy)propoxy]-2,3-naphthalene-diol of the formula

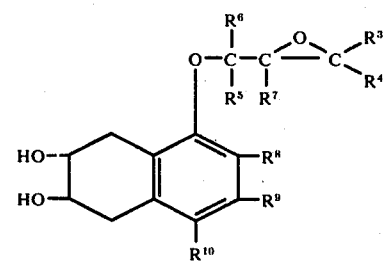

by reacting a naphthalenetriol of formula XI with an alkali metal alkoxide (e.g., sodium methoxide) in an alcohol solvent boiling below about 100° C (e.g., methanol) under nitrogen, and then, after removal of the solvent, stirring the residue in a dipolar aprotic solvent such as dimethylsulfoxide, hexamethylphosphoramide or dimethylformamide, with an epoxide having the formula

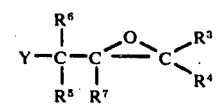

under nitrogen.

The 2,3-trans-1,2,3,4,-tetrahydro-5-[2,3-(epoxy)-propoxy]-2,3-naphthalenediol of formula XII is then reacted with an alkylamine having the formula $H_2N-R^1$ (XIV)

to form 2,3-trans-1,2,3,4-tetrahydro-5-[2-hydroxy-3-(alkylamino)-propoxy]-2,3-naphthalenediol of formula II.

The corresponding cis isomer of formula II can be prepared by dissolving a dihydronaphthalene acetate of formula X in acetic acid and water (from 92 to 98% acetic acid, preferably 96% acetic acid), and then treating the solution with silver acetate and iodine and heating under nitrogen (as described for the preparation of the trans-isomer) to form the cis-5,6,7,8-tetrahydro-1,6,7-naphthalenetriol having the formula

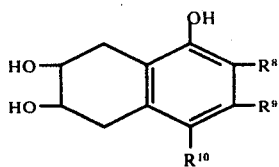

XV after basic hydrolysis. A compound of formula XV can be converted to the 2,3-cis-1,2,3,4-tetrahydro-5-[2,3-(epoxy)propoxy]-2,3-naphthalenediol, which in turn can be converted to the 2,3-cis-1,2,3,4-tetrahydro-5-[2-hydroxy-3-(alkylamino)-propoxy]-2,3-naphthalenediol in a manner similar to that described with respect to the preparation of the corresponding trans isomer.

Alternatively, the 2,3-trans-1,2,3,4-tetrahydro-5-[2-hydroxy-3-(alkylamino)propoxy]-2,3-naphthalenediol of formula II can be prepared from a 5,8-dihydro-1-naphthol of formula IX by mixing a cooled solution (temperature less than about 30° C) of 5,8-dihydro-1-naphthol in ethyl acetate with m-chloroperbenzoic acid and mixing the resulting slurry with a mixture of ethyl ether and aqueous sodium bicarbonate, to form a 5,6,7,8-tetrahydro-6,7-epoxy-1-naphthol having the formula

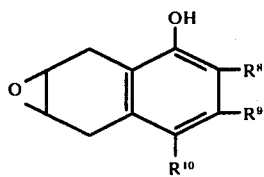

XVI

A 5,6,7,8-tetrahydro-6,7-epoxy-1-naphthol of formula XVI in tetrahydrofuran can be reacted with aqueous perchloric acid at a temperature within the range of from about 0 to about 60° C, to form a trans-5,6,7,8-tetrahydro-1,6,7-naphthalenetriol or formula XI which can be converted to the corresponding 2,3-trans-1,2,3,4-tetrahydro-5-[2,3-(epoxy)propoxy]-2,3-naphthanediol of formula XII, which in turn can be converted to the corresponding 2,3-trans-1,2,3,4-tetrahydro-5-[2-hydroxy-3-(alkylamino)propoxy]-2,3-naphthalenediol of formula II using the procedures described above.

The following examples further illustrate the invention.

EXAMPLE 1

5-[3-[(1,1-Dimethylethyl)amino]-2-hydroxypropoxy]-1,2,3,4-tetrahydro-cis-2,3-naphthalalenediol, diacetate ester, hydrochloride (1:1)

(a). cis-5,6,7,8-Tetrahydro-1,6,7-naphthalenetriol

A solution of 29.2 g. of 5,8-dihydro-1-naphthol and 40ml of acetic anhydride in 100ml of pyridine is prepared. After 16 hours the solvent is removed in vacuo and the residue is dissolved in ether and washed with 200ml of 5% hydrochloric acid, water, 200ml of 10% sodium hydroxide, saturated salt solution and dried. Solvent removal gives 34.2g of crude acetate which is dissolved in 900ml of acetic acid and 36ml of water. Silver acetate (53.3g) is added followed by 40.6g of iodine. The slurry is heated with good stirring at 85±10° C for 3 hours under nitrogen, cooled and filtered. The filtrate is evaporated in vacuo and the residue dissolved in 250ml of methanol and cooled to 0° C. A solution of 40g of sodium hydroxide in 200ml of water is added under nitrogen and the mixture is stirred overnight. The bulk of the methanol is removed in vacuo whereupon a solid forms. The solid is separated by filtration, dissolved in 150ml of water and acidified with 20ml of concentrated hydrochloric acid. Cooling gives a solid which is filtered and dried to give 16.5g cis-5,6,7,8-tetrahydro-1,6,7-naphthalenetriol melting point 184.5°–187° C. Three recrystallizations from absolute ethanol give the analytical sample, melting point 188°–188.5° C.

(b).
2,3-cis-1,2,3,4-Tetrahydro-[5-[2,3-(epoxy)propoxy]-2,3-naphthalenediol

A solution of 1.20g of sodium methoxide and 5.4g of cis-5,6,7,8-tetrahydro-1,6,7-naphthalenetriol in 200ml of methanol is prepared under nitrogen. The residue obtained upon solvent removal is stirred overnight with 200ml of dimethylsulfoxide and 4.65g of epichlorohydrin under nitrogen. The bulk of the solvent is removed at 50° C at 0.1mm and the residue is dissolved in 100ml of water. Extraction with chloroform (ten 200ml portions) gives a solid which is recrystallized from 150ml of hexane-ethyl acetate to give the title compound.

(c).
2,3-cis-1,2,3,4-Tetrahydro-5-[2-hydroxy-3-(tert-butylamino)propoxy]-2,3-naphthalenediol A mixture of 3.0g of 2,3-cis-1,2,3,4-tetrahydro-5-[2,3-(epoxy)propoxy]-2,3-naphthalenediol (melting point 104°–107° C, one spot on TLC--alumina, 5% methanol in chloroform, iodine visualization) and 22ml of t-butylamine is heated at 85°–95° C for 15 hours in a Parr bomb and the excess amine is removed in vacuo. The solid obtained by trituration of the residue with ether is filtered and recrystallized from benzene to give 3.4g of the title compound, melting point 124°–136° C.

(d).
2,3-cis-5-[[3-(1,1-Dimethylethyl)-2-phenyl-5-oxazolidinyl]methoxy]-1,2,3,4-tetrahydro-2,3-naphthalenediol Benzaldehyde (26.6g) is added to a suspension of 15.5g of 2,3-cis-1,2,3,4-tetrahydro-5-(2-hydroxy-3-(tert-butylamino)-propoxy]-2,3-naphthalenediol in 400ml of xylene, and the mixture is stirred at reflux for 48 hours with a Dean-Stark trap in the system. The solvent is removed in vacuo to give 20g of dense oil residue. The material is chromatographed on 300g of neutral Alumina III to give 1.1g of forerun (benzaldehyde) eluted with benzene; and 10.5g of the title compound product eluted with 50–100% chloroform-benzene and 5% methanol-chloroform.

(e).
2,3-cis-5-[[3-(1,1-Dimethylethyl)-2-phenyl-5-oxazolidinyl]methoxy]-1,2,3,4-tetrahydro-2,3-naphthalenediol, diacetate ester Acetic anhydride (8.8g) is added to a solution of 10.5g of 2,3-cis-[[3-(1,1-dimethylethyl)-2-phenyl-5-oxazolidinyl]methoxy]-1,2,3,4-tetrahydro-2,3-naphthalenediol in 150ml of dry pyridine and the solution is stirred for 6 hours at room temperature. The solution is diluted with 4ml of methanol, stirred for 10 minutes and then evaporated in vacuo. The residue is chromatographed on 200g of neutral Alumina III eluted with 1:1 ethyl acetate-hexane. The diacetate product (4.6g) is obtained in the initial 200ml of eluent. An additional 400ml of eluent gives 4.7g of material which appears to be the mono-acetylated intermediate. The latter material is further treated with acetic anhydride-pyridine for 18 hours, to give, on workup, 5.0g of the desired diacetate. This is combined with the 4.6g of diacetate from the column to give 9.6g of the title compound.

(f).
5-[3-[(1,1-Dimethylethyl)amino]-2-hydroxypropoxy]-1,2,3,4-tetrahydro-cis-2,3-naphthalenediol, hydrochloride (1:1)

Palladium on carbon (8g, 5%) is added to a solution of 8.4g of 2,3-cis-[[3-(1,1-dimethylethyl)-2-phenyl-5-oxazolidinyl]-methoxy]-1,2,3,4-tetrahydro-2,3-naphthalenediol, diacetate ester in 500ml of absolute ethanol and the mixture placed on a Parr shaker under 54 psi of hydrogen for 23 hours. The mixture is filtered, the catalyst washed with 150ml of absolute ethanol, and the combined filtrates evaporated in vacuo to give 6.5g of crude product. Chromatography on 150g of neutral Alumina III gives 3.5g of forerun material (eluted with 650ml of 40–75% chloroform in benzene) and then 2.4g of the desired product (eluted with 75–100% chloroform in benzene). The product is converted to its hydrochloride salt and recrystallized from isopropanolether to give 1.4g of the title compound, melting point 170°–197° C.

EXAMPLES 2–7

Following the procedure of Example 1, but substituting the compound listed in column I for 5,8-dihydro-1-naphthol, the compound listed in column II for t-butylamine, and the compound listed in column III for the acetic anhydride acylating agent in Example 1(e), yields the compound listed in column IV.

ethyl acetate. After 16 hours at ambient temperature the slurry is poured into a cooled, stirred mixture of 300ml each of ether and 10% sodium bicarbonate. After 15 minutes the organic phase is separated, washed with water, saturated salt solution and dried. Solvent removal gives an oil which is triturated with two 100ml portions of boiling hexane. The residue is recrystallized from 150ml of 1:1 hexane-ethyl acetate to give 6.6g of 5,6,7,8-tetrahydro-6,7-epoxy-1-naphthol, melting point 143°–146° C. Two further recrystallizations of a small sample give the analytical sample melting point 149.5°–151° C.

(b). trans-5,6,7,8-Tetrahydro-1,6,7-naphthalenetriol

A solution of 8.0g of 5,6,7,8-tetrahydro-6,7-epoxy-1-naphthol in 100ml of tetrahydrofuran is cooled to 0° C and 20ml of water and 0.5ml of 70% perchloric acid are added. After 4 hours, a further 1.5ml of acid is added and the solution is stirred for 16 hours at ambient temperature and diluted with 100ml each of ether, 10% sodium bicarbonate and saturated salt solution. The aqueous layer is separated and washed with 150ml of 1:1 ether-tetrahydrofuran. The organic phase is washed with saturated salt solution, dried and evaporated to give an oil which solidifies on trituration with chloroform. Recrystallization gives in two crops, 4.85g of solid which is recrystallized from ethyl acetate to give 3.84g, melting point 179.5°–181.5° C. Two further recrystallizations of a small sample give the analytical specimen, melting point 183°–184° C.

(c).
2,3-trans-1,2,3,4-Tetrahydro-5-[2,3-(epoxy)-propoxy]-2,3-naphthalenediol

A solution of 3.60g of trans-5,6,7,8-tetrahydro-1,6,7-naphthalenetriol in 100ml of methanol is cooled to 0° C and 1.08g of sodium methoxide in methanol is added. The solvent is removed in vacuo and the residue heated

| Example | Column I | Column II | Column III | Column IV |
|---|---|---|---|---|
| 2 | 5,8-dihydro-1-naphthol | isopropylamine | lauric anhydride | 5-[2-hydroxy-3-(isopropylamino)propoxy]-1,2,3,4-tetrahydro-cis-2,3-naphthalenediol, dilaurate ester, hydrochloride |
| 3 | 5,8-dihydro-1-naphthol | ethylamine | benzoic anhydride | 5-[3-(ethylamino)-2-hydroxypropoxy]-1,2,3,4-tetrahydro-cis-2,3-naphthalenediol, dibenzoate ester, hydrochloride |
| 4 | 5,8-dihydro-1-naphthol | n-octylamine | o-toluic anhydride | 5-[2-hydroxy-3-(n-octylamino)propoxy]-1,2,3,4-tetrahydro-cis-2,3-naphthalenediol, di-(o-toluate)ester, hydrochloride |
| 5 | 5,8-dihydro-3-methoxy-1-naphthol | t-butylamine | p-nitrobenzoic anhydride | 5-[3-(t-butylamino)-2-hydroxypropoxy]-7-methoxy-1,2,3,4-tetrahydro-cis-2,3-naphthalenediol, di-(p-nitrobenzoate)-ester, hydrochloride |
| 6 | 5,8-dihydro-3-methyl-1-naphthol | isopropylamine | phenylacetic anhydride | 5-[2-hydroxy-3-(isopropylamino)propoxy]-7-methyl-1,2,3,4-tetrahydro-cis-2,3-naphthalenediol, di-(phenylacetate)-ester, hydrochloride |
| 7 | 5,8-dihydro-2-cyclopropyl-1-naphthol | t-butylamine | 3-(p-chlorophenyl)-butanoic anhydride | 6-cyclopropyl-5-[3-(t-butylamino)-2-hydroxypropoxy]-1,2,3,4-tetrahydro-cis-2,3-naphthalenediol, di-[3-(p-chlorophenyl)butanoate]ester, hydrochloride |

EXAMPLE 8

5-[2-Hydroxy-3-(isopropylamino)propoxy]-1,2,3,4-tetrahydrotrans-2,3-naphthalenediol, diacetate ester (a). 5,6,7,8-Tetrahydro-6,7-epoxy-1-naphthol An amount of 25.0g of m-chloroperbenzoic acid is added over 10 minutes to an ice-cooled solution of 14.6g of 5,8-dihydro-1-naphthol (prepared as described in Org. Syn., Coll. Vol. IV. pg. 887) in 225ml of at 50° C at 0.05mm for 1 hour, dissolved in 80ml of dimethylsulfoxide and stirred overnight under nitrogen with 3.68g of epichlorohydrin. After 17 hours, the solvent is removed in vacuo, and the residue is dissolved in 250ml of water and extracted three times with 150ml of ether and two times with 150ml of chloroform. Both organic extracts are washed with excess 5% sodium hydroxide, saturated salt solution and dried. Solvent removal gives a total of 3.25g of solid which is recrystallized from benzene to give 2.59g of the title compound, melting point 113°–116° C.

(d).

2,3-trans-1,2,3,4-Tetrahydro-5-[2-hydroxy-3-(isopropylamino)propoxy]-2,3-naphthalenediol A solution of 2.5g of 2,3-trans-1,2,3,4-tetrahydro-5-[2,3-(epoxy)-propoxy]-2,3-naphthalenediol in 15ml of isopropylamine is heated at 80° C± 5° for 16 hours in a Parr bomb (pressure = 40 lb/in$^2$). The solution is evaporated in vacuo to give a foam which crystallizes on trituration with ether. Filtration gives 2.96g which is recrystallized three times from benzene to give 2.06g of the title compound, melting point 112°–127° C.

(e).

2,3-trans-5-[(3-isopropyl-2-phenyl-5-oxazolidinyl)methoxy]-1,2,3,4-tetrahydro-2,3-naphthalenediol Benzaldehyde (0.025mole) is added to a suspension of 2,3-trans-1,2,3,4-tetrahydro-5-[2-hydroxy-3-(isopropylamino)propoxy]-2,3-naphthalenediol (0.005mole) in 50ml of xylene, and the mixture is stirred at reflux for 48 hours with a Dean-Stark trap in the system. The solvent is removed in vacuo to yield the title compound.

(f).

2,3-trans-5-[(3-isopropyl-2-phenyl-5-oxazolidinyl)methoxy]-1,2,3,4-tetrahydro-2,3-naphthalenediol, diacetate ester Acetic anhydride (0.008mole) is added to a solution of (0.005mole) in 20ml of dry pyridine and the solution is stirred for 6 hours at room temperature. The solution is diluted with 4ml of methanol, stirred for 10 minutes and then evaporated in vacuo to yield the title compound.

(g).

5-[2-hydroxy-3-(isopropylamino)propoxy]-1,2,3,4-tetrahydro-2,3-cis-naphthalenediol, diacetate ester Palladium on carbon (0.8g, 5%) is added to a solution of 2,3-trans-5-[(3-isopropyl-2-phenyl-5-oxazolidinyl)methoxy]-1,2,3,4-tetrahydro-2,3-naphthalenediol, diacetate ester (0.002mole) in 50ml of absolute ethanol and the mixture is placed on a Parr shaker under 54 psi of hydrogen for 23 hours. The mixture is filtered, the catalyst washed with 150ml of absolute ethanol, and the combined filtrates evaporated in vacuo to give the title compound.

What is claimed is:

1. A compound having the formula

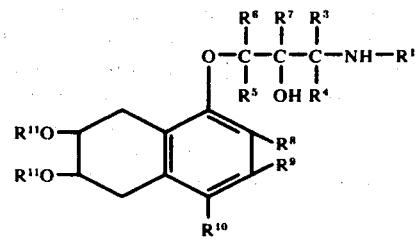

or a pharmaceutically acceptable salt thereof, wherein $R^1$ is lower alkyl; $R^3$, $R^4$, $R^5$, $R^6$ and $R^7$ are the same or different and are hydrogen or lower alkyl; $R^8$, $R^9$ and $R^{10}$ are the same or different and are hydrogen, lower alkyl, lower alkoxy, or monocyclic cycloalkyl having 3 to 6 carbon atoms; and $R^{11}$ is an acyl group of the type

wherein n is an integer of from 1 to 11,

wherein X is monocyclic aryl, or

wherein Z is monocyclic aryl-lower alkyl; wherein lower alkyl and lower alkoxy are groups having 1 to 8 carbon atoms and monocyclic aryl is phenyl, lower alkyl phenyl, di(lower alkyl)-phenyl, halophenyl, nitrophenyl, dinitrophenyl, or trinitrophenyl.

2. A compound in accordance with claim 1 wherein $R^3$, $R^4$, $R^5$, $R^6$, $R^7$, $R^8$, $R^9$ and $R^{10}$ are hydrogen.

3. A compound in accordance with claim 2 wherein $R^1$ is isopropyl.

4. A compound in accordance with claim 3 wherein $R^{11}$ is

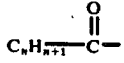

5. A compound in accordance with claim 3 wherein $R^{11}$ is

6. A compound in accordance with claim 3 wherein $R^{11}$ is

* * * * *

UNITED STATES PATENT OFFICE
CERTIFICATE OF CORRECTION

Patent No. 4,029,676      Dated June 14, 1977

Inventor(s) Frederic P. Hauck et al.

It is certified that error appears in the above-identified patent and that said Letters Patent are hereby corrected as shown below:

Column 3, first structure should read:

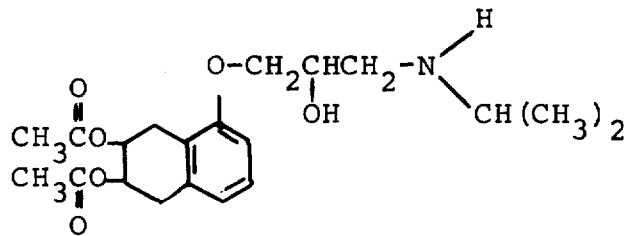

Claim 4, the structure should read:

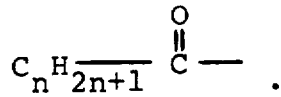

Signed and Sealed this

Eighth Day of November 1977

[SEAL]

Attest:

RUTH C. MASON  
Attesting Officer

LUTRELLE F. PARKER  
Acting Commissioner of Patents and Trademarks